(12) United States Patent
Tipirneni

(10) Patent No.: US 7,180,624 B2
(45) Date of Patent: Feb. 20, 2007

(54) SYSTEMS AND METHODS FOR REMOTE VIEWING OF PATIENT IMAGES

(75) Inventor: Kishore Tipirneni, Glendale, AZ (US)

(73) Assignee: Stryker Corporation, Kalamazoo, MI (US)

( * ) Notice: Subject to any disclaimer, the term of this patent is extended or adjusted under 35 U.S.C. 154(b) by 518 days.

(21) Appl. No.: 10/766,232

(22) Filed: Jan. 28, 2004

(65) Prior Publication Data

US 2004/0257608 A1   Dec. 23, 2004

Related U.S. Application Data

(63) Continuation of application No. 10/029,817, filed on Dec. 13, 2001, now Pat. No. 6,798,533, which is a continuation of application No. 09/219,956, filed on Dec. 13, 1998, now Pat. No. 6,381,029.

(51) Int. Cl.
    *G06K 15/00*   (2006.01)
(52) U.S. Cl. ............... 358/1.15; 358/468; 358/406; 709/217; 709/219
(58) Field of Classification Search ........... 358/400, 358/403, 1.14, 1.12, 1.15, 1.9, 1.5, 2.1, 405, 358/406, 504, 468; 709/217, 219
See application file for complete search history.

(56) References Cited

U.S. PATENT DOCUMENTS

| | | | |
|---|---|---|---|
| 4,817,050 A | | 3/1989 | Komatsu et al. |
| 4,910,609 A | * | 3/1990 | Nicholas et al. ............ 382/232 |
| 5,179,651 A | | 1/1993 | Taaffe et al. |
| 5,291,401 A | | 3/1994 | Robinson |
| 5,321,520 A | | 6/1994 | Inga et al. |
| 5,384,643 A | | 1/1995 | Inga et al. |
| 5,416,602 A | | 5/1995 | Inga et al. |
| 5,469,353 A | * | 11/1995 | Pinsky et al. ............... 382/131 |
| 5,715,823 A | | 2/1998 | Wood et al. |
| 5,802,518 A | * | 9/1998 | Karaev et al. ................. 707/9 |
| 5,810,747 A | * | 9/1998 | Brudny et al. .............. 600/595 |
| 5,815,156 A | | 9/1998 | Takeuchi |
| 6,064,490 A | * | 5/2000 | Minamizawa .............. 358/1.14 |
| 6,101,536 A | * | 8/2000 | Kotani et al. ............... 709/217 |
| 6,157,675 A | * | 12/2000 | Mitsuhashi et al. ..... 375/240.01 |
| 2001/0011301 A1 | * | 8/2001 | Sato et al. ................. 709/219 |
| 2001/0032246 A1 | * | 10/2001 | Fardella et al. ............ 709/206 |

FOREIGN PATENT DOCUMENTS

| | | |
|---|---|---|
| EP | 0 844 581 A2 | 5/1998 |
| EP | 0 844 781 A2 | 5/1998 |

* cited by examiner

*Primary Examiner*—Jerome Grant, II
(74) *Attorney, Agent, or Firm*—Snell & Wilmer L.L.P.

(57) ABSTRACT

A digital camera containing patient images is connected to an uploader computer and the patient's name or history is entered into the uploader computer. The uploader computer then connects to the Internet, connects to the secure host server, uploads the images to the host server and shuts down the Internet connection. After the physician selects a medical facility and the system verifies the physician's user I.D. and password, the host server constructs an HTML web page which includes a list of patients whose images were previously uploaded by the medical facility and are available for viewing The physician simply selects the name of a patient and the host server displays the patient information and images on the physician's computer. The system is password-protected at all levels and the operator for each medical facility determines who may have access to the medical facility images.

13 Claims, 10 Drawing Sheets

SYSTEMS AND METHODS FOR REMOTE VIEWING OF PATIENT IMAGES

This application is a continuation of Ser. No. 10/029,817 filed Dec. 13, 2001 now U.S. Pat. No. 6,798,533 which is a continuation of Ser. No. 09/219,956 filed Dec. 23, 1998 now U.S. Pat. No. 6,381,029.

This application contains Microfiche Appendix, pursuant to 37 CFR 1.96 (MPEP 608.05), of a computer program listing printout of over ten pages.

BACKGROUND OF THE INVENTION

1. Technical Field

The present invention relates, generally, to systems and methods for remote viewing and, more particularly, to a password-protected system which acquires and transmits patient images to a server for remote access via the Internet.

2. Background Invention

A medical facility typically requires physician input to determine the most appropriate medical care for the patient. However, requiring a physician to be present 24 hours a day at the medical facility to examine the patient, or a radiological image of the patient, may be inefficient and expensive. Particularly, a medical facility may not have the financial resources or patient volume to support a physician on site at all times; the medical facility may be located in a remote location; or a town may not have a sufficient number of physicians available to be located at each medical facility at all times of the day. As such, when a patient requires medical attention, an experienced physician may not be readily available at a particular medical facility.

Accordingly, a system is needed which acquires an image of a patient and transmits the image to a remote location for viewing and analysis by an experienced physician. While prior art teleradiology systems exist which establish a direct communication link to a remote location and transmit radiological images to the remote location, these systems often require dedicated hardware and software at the medical facility and at the remote viewing location wherein the hardware and software is complicated and expensive. Due to increasing budget constraints, medical facilities and physicians typically cannot allocate the substantial funds required to purchase the dedicated teleradiology systems. Moreover, existing teleradiology systems do not provide secure, password-protected transmission of data from numerous medical facilities to a centralized repository for remote viewing by physicians from their existing personal computers.

With the rapid expansion of the Internet and other computer-based technologies, a personal computer already exists at a physician's home or office. Physicians are also becoming increasingly knowledgeable of computer technology, the use of a personal computer, and the use of information on the Internet. While the Internet allows the transmission of electronic mail with image attachments, the use of electronic mail is typically not secure and requires the entry of various Internet addresses in order to send an image to multiple locations. Moreover, many individual medical facilities have their own computer systems which can be accessed, via a user identification and password, by physicians associated with the medical facility. However, physicians are typically associated with a few medical facilities, thereby often requiring a physician to obtain, and keep track of, different user identifications and passwords to access each medical facility computer. Thus, a system is needed which allows physicians to use a single user identification and password for viewing patient images from a home or office, in a secure manner, over the Internet.

BRIEF SUMMARY OF THE INVENTION

To upload images, a person at the medical facility simply takes pictures of the patient or the patient's radiological scan with a digital camera which instantly digitizes the patient images. The digital camera is then connected to the uploader computer and the patient's name or history is entered into the uploader computer. The uploader program in the uploader computer automatically obtains the images from the digital camera and generates a data file, which includes the digitized images and any other patient information. The uploader computer then connects to the Internet, connects to the secure host server, uploads the images to the host server and shuts down the Internet connection. All of the operations are automatic, so the person at the medical facility does not need to wait by the computer while images are being uploaded. The system is password-protected at all levels and the administrator for each medical facility determines who may have access to the medical facility images.

When the physician uses an Internet compatible computer, the physician simply logs on to the host website which displays a list of medical facilities. Upon selection of a particular medical facility, the website requests entry of the physician's user I.D. and password. After verifying the physician's user I.D. and password, the host server constructs an HTML web page then displays the web page which includes a list of patients whose images were previously uploaded by the medical facility and are available for viewing. The physician simply selects the name of a patient and the host server displays the patient information and images on the physician's computer.

BRIEF DESCRIPTION OF THE DRAWING FIGURES

The subject invention will herein be described in conjunction with the appended drawing figures, wherein like numerals denote like elements, and:

DETAILED DESCRIPTION OF THE INVENTION

The present system and method generally allows the remote viewing over the Internet of patient images which are uploaded from a medical facility. The present invention may used in association with hospitals, clinics, emergency rooms, film rooms, x-ray facilities, medical offices, sports facilities and/or the like. Other users of the present invention need not be in the medical field. For example, any business or organization which requires a secure, password-protected depository on the Internet for the exclusive viewing of documents, images, text and/or the like by only authorized users is also contemplated within the scope of the present invention.

Figure 1:
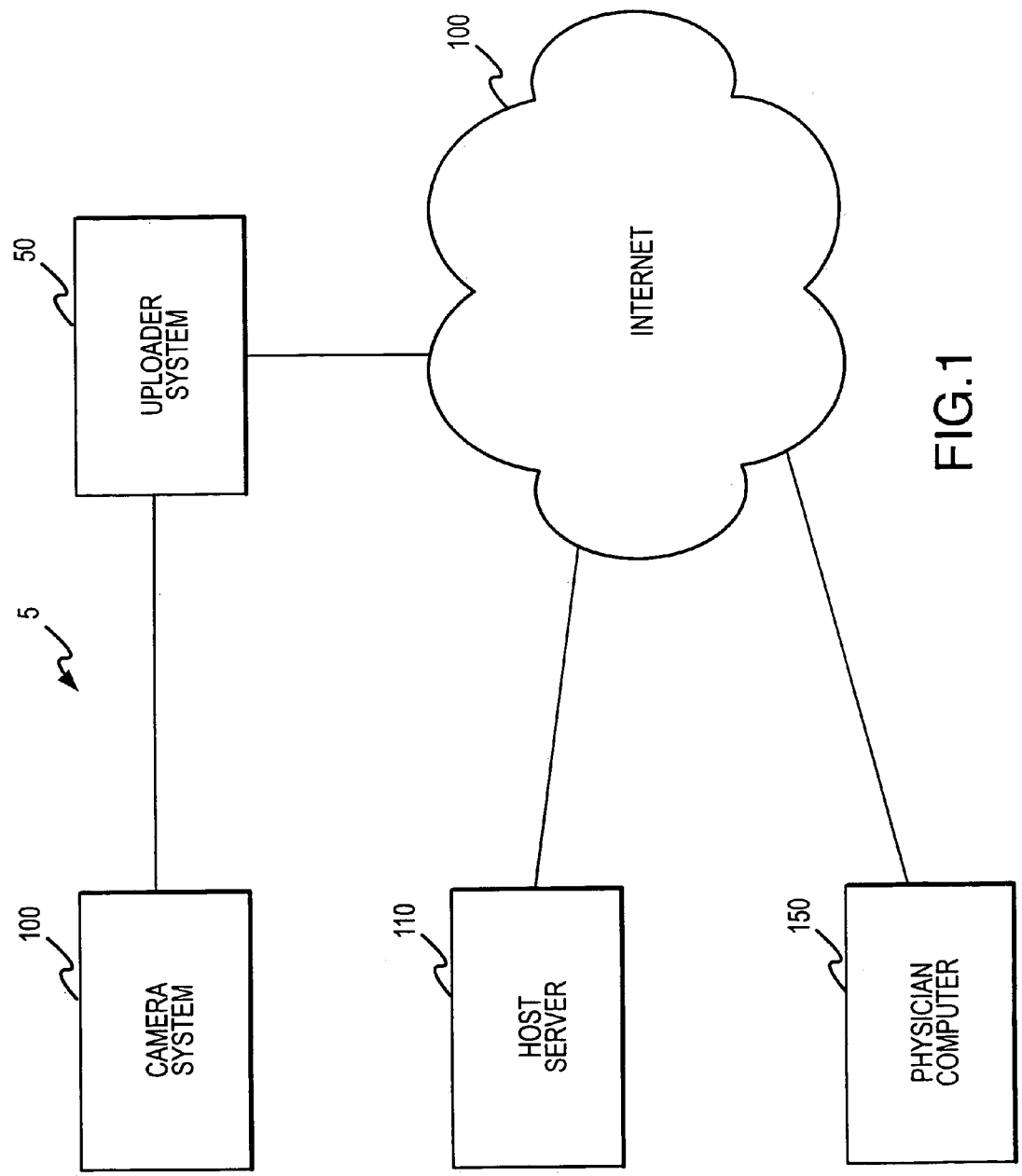
FIG. 1 is an exemplary schematic diagram of a simplified image retrieval and viewing system.
Figure 7:
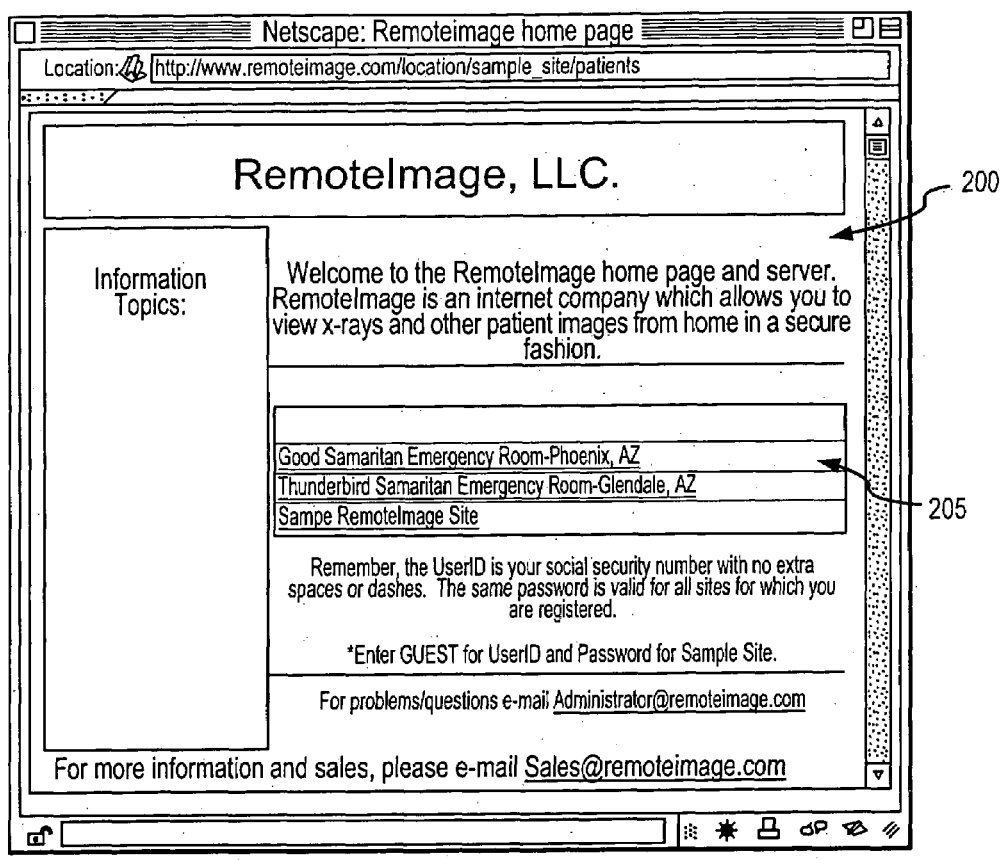
FIG. 7 shows an exemplary screen display of the home page on the physician computer while connected to the host website.
Figure 8:
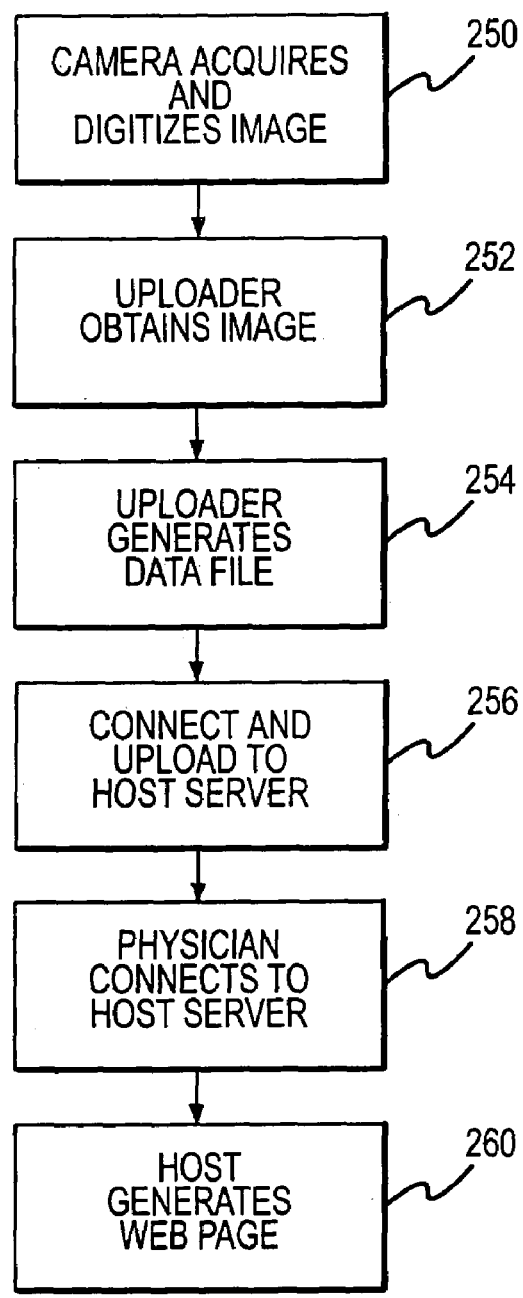
FIG. 8 shows an exemplary flow diagram of the process for acquiring, uploading and viewing patient images.

Referring to FIG. 1, system 5 preferably includes a camera system 10, an uploader system 50, an Internet 100, a host server 110 and a physician computer 150. In a preferred embodiment, referring to FIGS. 1 and 8 system 5 includes a unique process for acquiring, uploading and viewing patient images. To upload images, camera system 10 suitably acquires and digitizes the image (step 250) then uploader system 50 automatically obtains the image from camera system 10 (step 252). Uploader system 50 generates a data file including the patient image and patient information (step 254) then uploader system 50 connects to Internet 100 and uploads the images and associated information to host server 110 (step 256). The physician, using physician computer 150, suitably accesses Internet 100 and logs on to the host website 200 (FIG. 7) located on host server 110 (step 258). After suitable verification, host server 110 generates a web page (step 260), including the data file image and patient information, which is transmitted to physician computer 50 for the physician to view the images of particular patients. One skilled in the art will appreciate that communication between uploader system 50, host server 110 and physician computer 150 can also be achieved using a local area network or other similar communication systems in accordance with the present invention. Because the present invention preferably incorporates existing communication channels over the Internet and commonly available camera systems 100, uploader systems 50 and physician computers 150, the system is less expensive than other teleradiology systems, requires no specialized training and is upgradable as the respective technologies improve.

Figure 2:
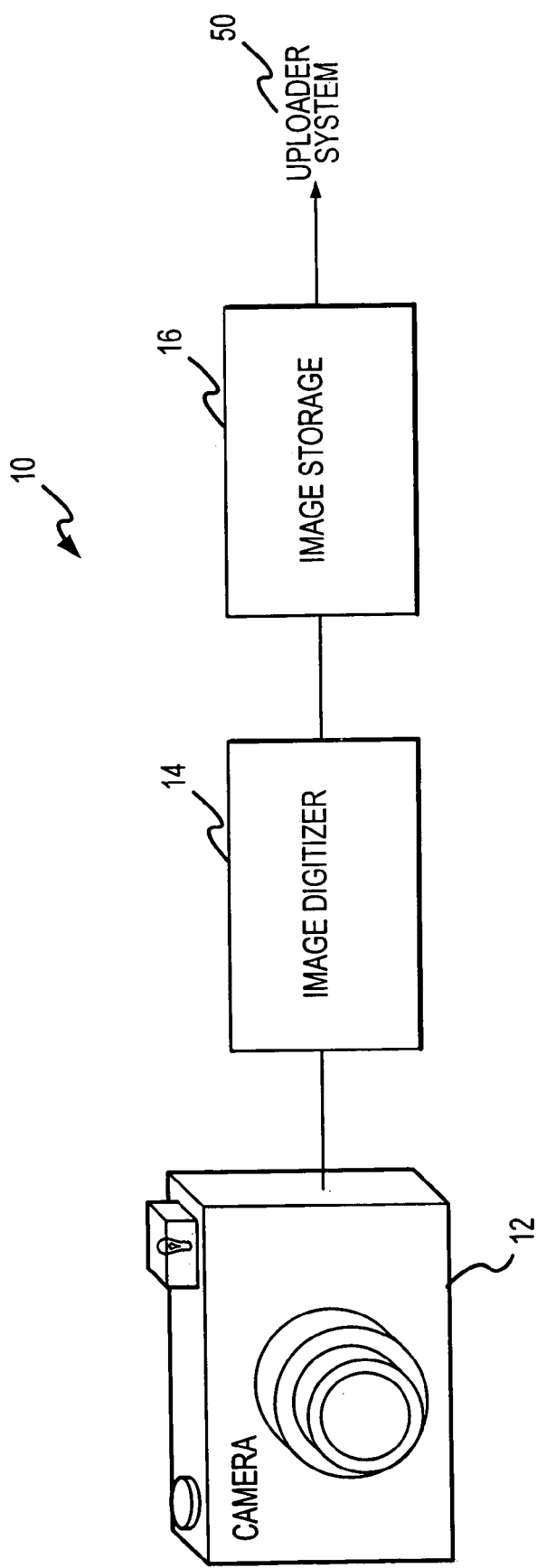
FIG. 2 is an exemplary schematic diagram of the camera system in greater detail.

Camera system 10 is any device or combination of devices suitably configured to acquire an image, digitize an image and transmit the digital image to uploader system 50. One of ordinary skill in the art will appreciate that camera system 10 can acquire any image in accordance with the present invention including, for example, x-rays, MR images, CT images or any other radiological image or a direct picture of patient pathology, wounds, lacerations, cellulitus, rashes, labs, EKGs, documents or any other information or subject capable of being photographed by a camera. Referring to FIG. 2, in a preferred embodiment, camera system 10 includes a digital camera 12, an image digitizer 14, an image storage buffer 16 and other known hardware and software components and electronics for suitable operation of a digital camera. One of ordinary skill in the art will appreciate that camera 12, image digitizer 14 and image storage 16 can be separate components or incorporated into a single digital camera device. Moreover, image digitizer 14 is any suitable device for digitizing an image such as, for, example, a camera which acquires the image in digital form, an analog-to-digital convertor and/or the like. Alternatively, uploader system 50 can include the digitizing component. In a preferred embodiment of the present invention, camera system 10 comprises a Sony® DSC-F1 digital camera manufactured by the Sony® Corporation.

After one or a plurality of images are obtained using camera system 10, camera system 10 is suitably connected to uploader system 50 to allow the transmission of the JPEG file images, stored in image storage 16, to uploader system 50. It is understood that camera system 10 digitizes the image before transmitting the image to uploader system 50; however, the present system also contemplates that uploader system 50 may digitize the image instead of camera system 10. Furthermore, camera system 10 may be permanently connected to uploader system 50, or preferably, camera system 10 is configured to be removably connected to uploader system 50 by a removable cable, thereby allowing camera system 10 to be freely manipulated to obtain close-up views of the patient image at almost any angle. Alternatively, camera system 50 may transmit the digital information to uploader system 50 via a signal, such as an infrared beam, without the 'need for a cable connection. Moreover, if camera 12 is connected to uploader system 50 during image retrieval, image storage 16 may not be necessary if the images are sent directly to uploader system 50.

Figure 3:
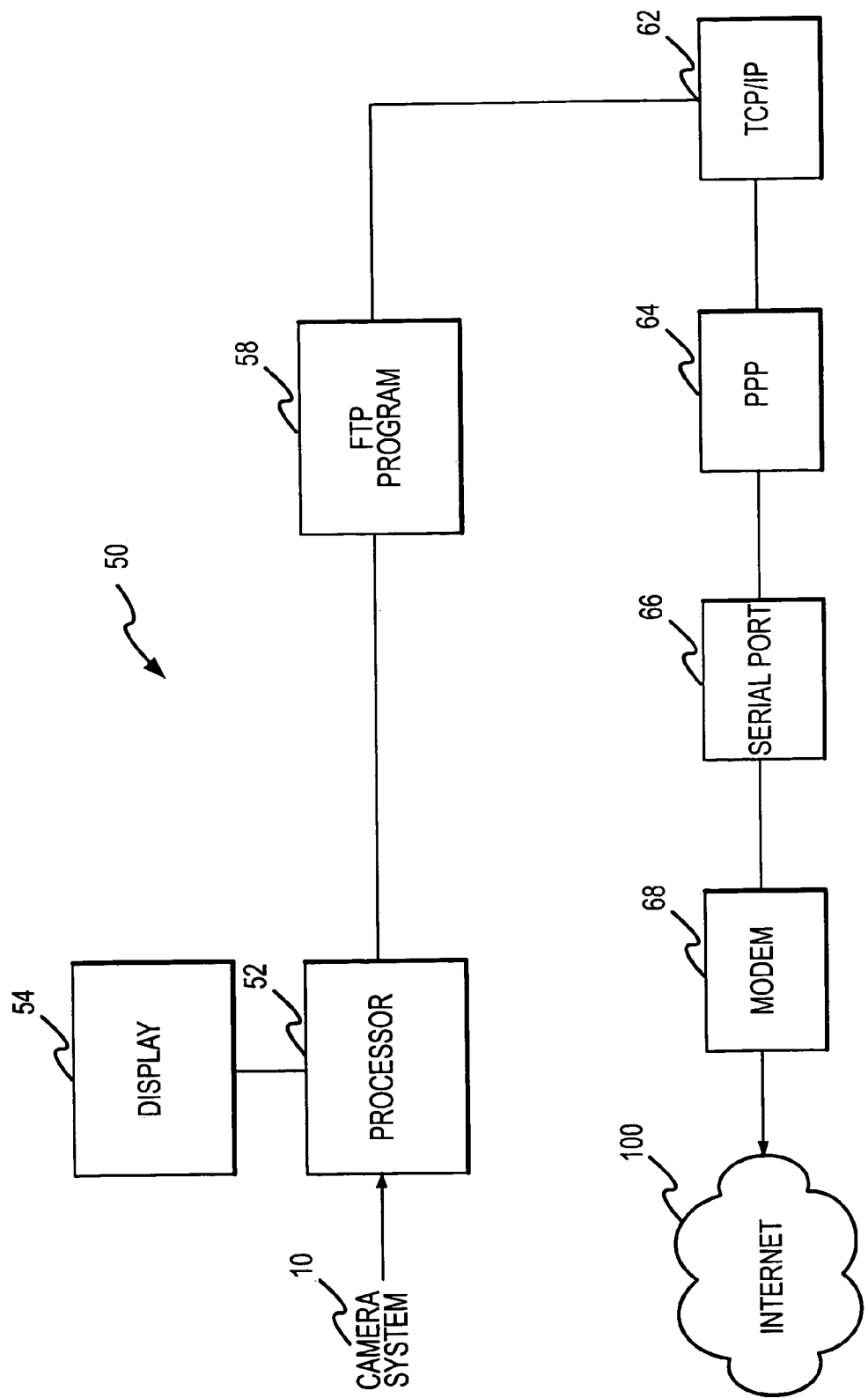
FIG. 3 is an exemplary schematic diagram of the uploader system in more detail.

Uploader system 50 is any device or combination of devices suitably configured to accept data from camera system 10 and generate a data file which includes the information from camera system 10. Uploader system 50 is also any system-which automatically connects to Internet 100, logs onto a host server 110 website, suitably uploads images to the website and shuts down the Internet connection. Uploader system 50 is preferably an Apple® iMAC® computer. Referring to FIG. 3, in a preferred embodiment, uploader system 50 includes processor 52, display 54, FTP program 58, TCP/IP 62, PPP 64, serial port 66, and modem 68. Processor 52 is any suitable central processing unit which executes a personal computer's software and displays the acquired images on display monitor 54. Processor 52 is also any suitable device capable of executing web browser software to access the Internet 100. In an alternative embodiment, system 5 includes numerous uploader systems 50 in which the individual processors 52 are networked to other processors through an Ethernet connection. Alternatively, TCP/IP 62 may be connected to a local network medium such as an Ethernet connection. In another embodiment, modem 68 is replaced with a direct connection to Internet 100. Moreover, one skilled in the art will appreciate that TCP/IP 62, PPP 64, serial port 66 and/or modem 68 can be multiple components, part of one system, internal to a computer, external devices or not required if a direct connection to the Internet is used.

Figure 5:
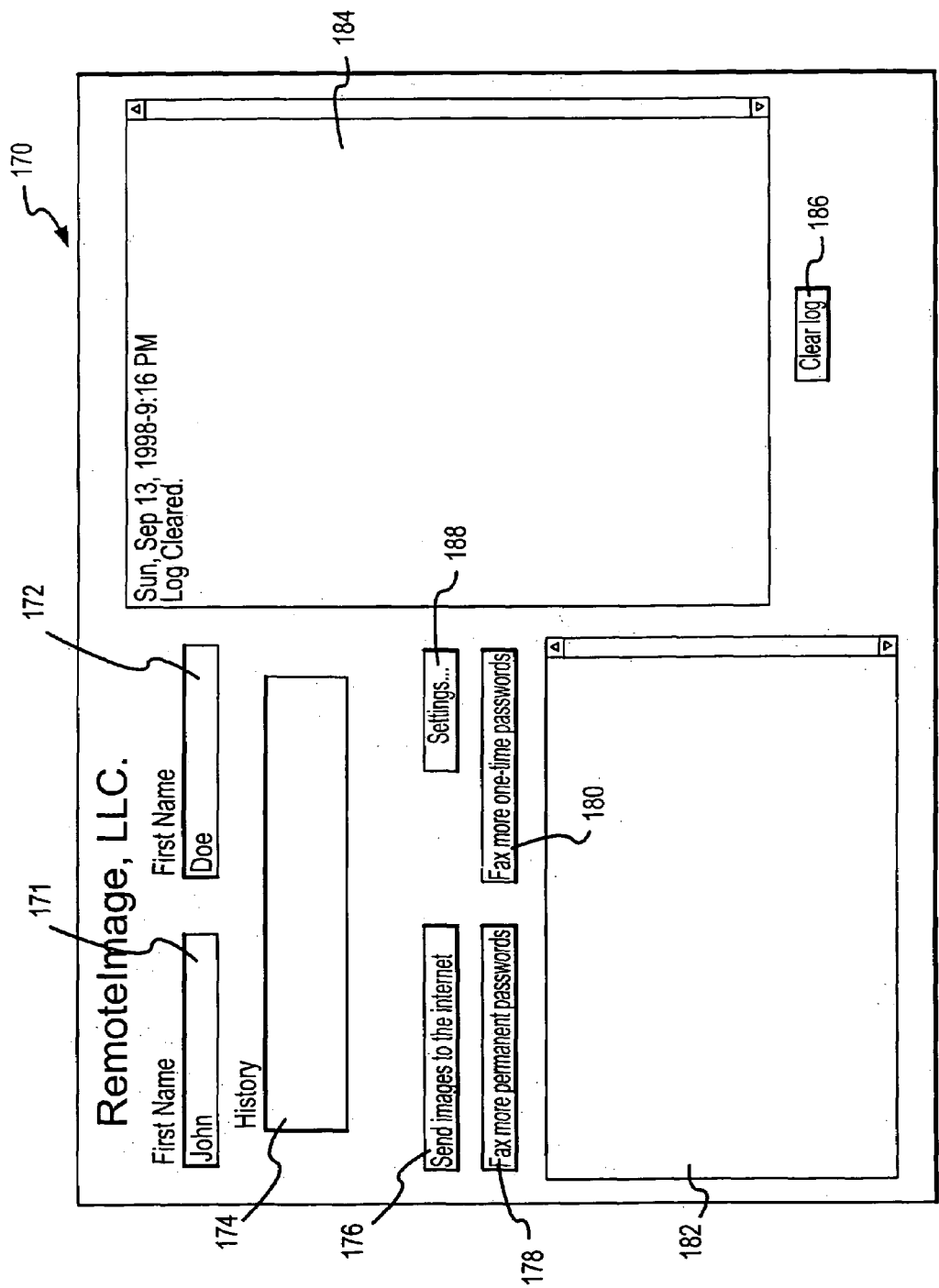
FIG. 5 shows an exemplary screen display of the uploader system.
Figure 6:
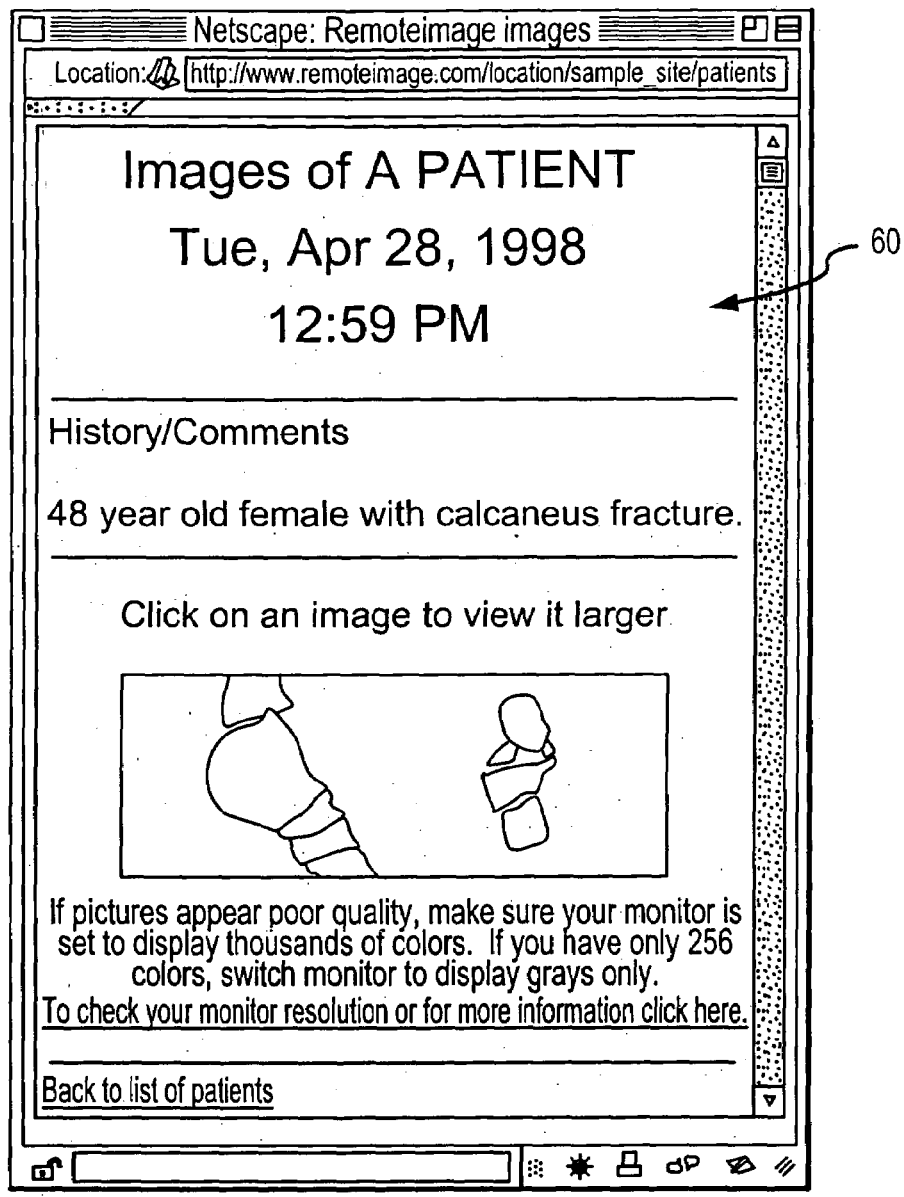
FIG. 6 shows an exemplary screen display of patient data on the physician computer while connected to the host website.

With reference to FIG. 5, the medical facility operator preferably interfaces with a screen display 170 of uploader system 50 which is a graphical user interface preferably including a first name field 171, a last name field 172, a history field 174, a Send Images to Internet Command 176, a Fax More Permanent Passwords Command 178, a Fax More One-time Passwords Command 180, an image field 182, a log field 184, a Clear Log Command 186 and a Settings Command 188. One skilled in the art will appreciate that screen display 170 can include other fields and commands to preform functions, display data or optimize other computer variables in accordance with the present invention.

Figure 9:
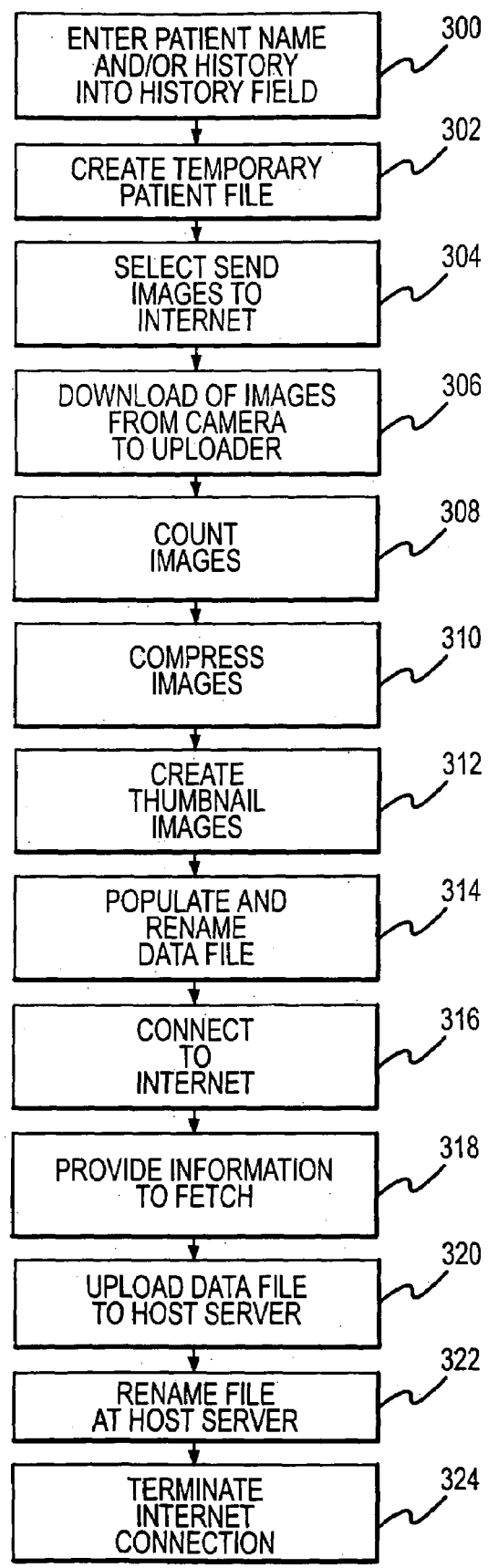
FIG. 9 shows an exemplary flow diagram of the process for uploading images from the uploader system to the host server; and, FIG. 10 shows an exemplary flow diagram of the process, for physician access to the patient images on the host server.
Figure 10:
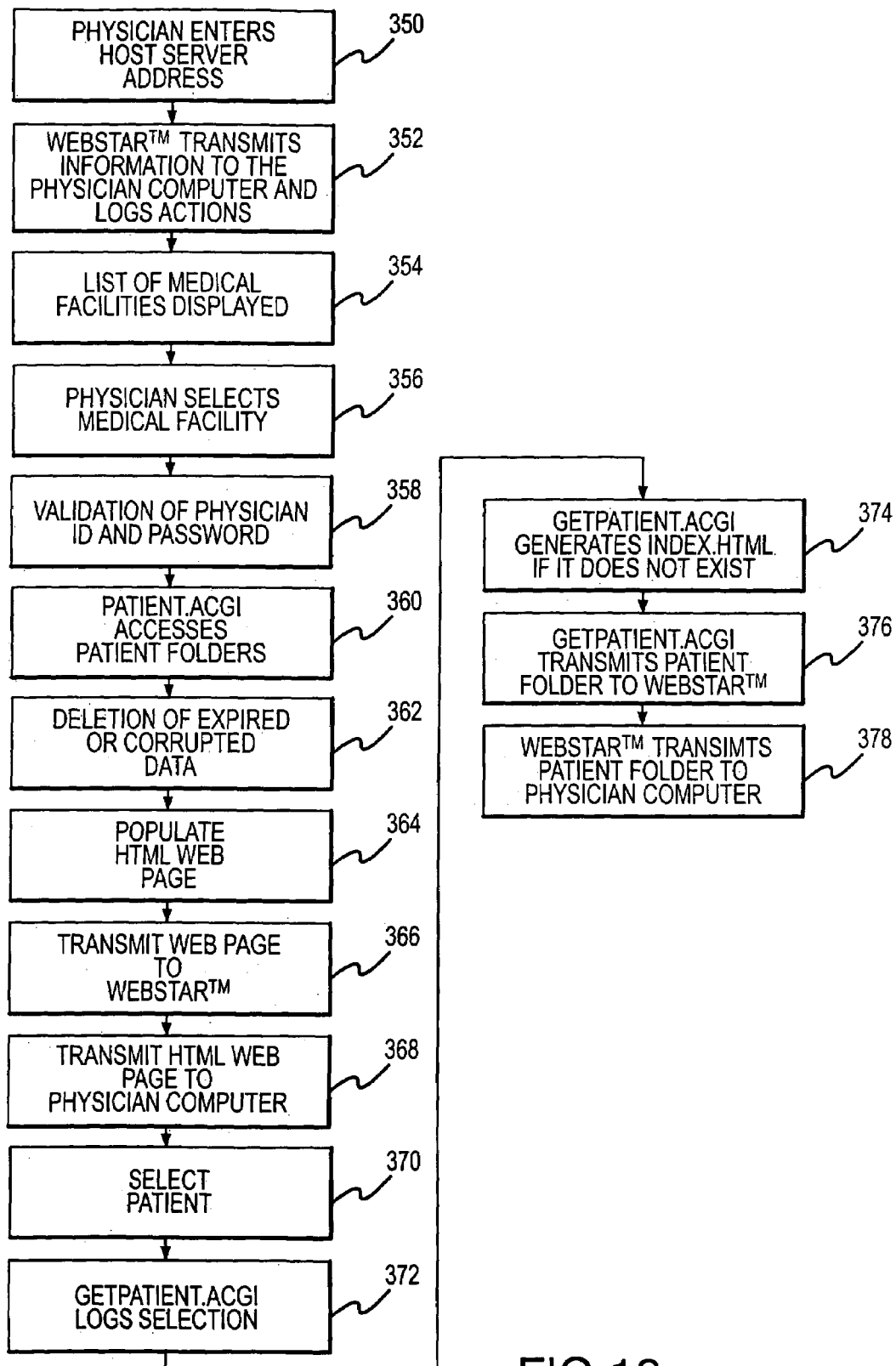

Referring to FIGS. 5 and 9, after connecting camera system 10 to uploader system 50, the medical facility operator enters a patient name into patent name fields 171, 172 and/or history associated with a particular patient into history field 174 (step 300). Processor 52 of uploader system 50 then creates a location on its hard drive with a temporary file name for the particular patient (step 302). After the operator selects the Send Images to Internet Command 176 (step 304), processor 52 automatically transmits a request for a download of all images from camera system 10 wherein the request includes the location of the temporary file on the hard drive in uploader system 50. In response to the request, camera system 10 suitably transmits the previously acquired images in JPEG format to uploader system 50 (step 306). In a preferred embodiment, camera system 10 includes known software which is configured to respond to the download request. Uploader system 50 preferably includes a macro which re-creates the downloading routine such that the downloading process is automatic after selection of the Send Images to Internet Command 176 by the operator. In a preferred embodiment, the macro QUICK-EYS™ produced by CE Software suitably provides the automatic re-creation of the downloading process.

After receiving the images, uploader system 50 suitably counts the number of images transmitted from camera system 10 (step 308). In a preferred embodiment, if the image data includes over 50K bytes of 640×480 pixel images, then processor 52 compresses the images using known compression routines before transmitting the images to host server 110 (step 310). If the image data includes under 50K bytes of 640×480 pixel images, then processor 52 preferably does not compress the images. One skilled in the art will appreciate that the threshold for implementing the compression routine or the image pixel dimensions can be changed to any desired quantity. Moreover, before transmitting the images to host server 110, processor 52 suitably creates "thumbnail" 128×96 pixel images of each image and displays the thumbnail images in image field 182 as the thumbnail images are processed (step 312). Uploader system 50 also suitably populates the previously created temporary data file with the aforementioned information, namely the number of images, patient name, current date and time, full images and thumbnail images. Uploader system 50 also renames the previously created data file with an exclamation point (!), patient name, time stamp and checksum (step 314). For example, the name of the data file could be "! Smith Robert 11:15PM E5".

Uploader system 50 then connects to the Internet 100 through modem 68 or through a direct connection between processor 52 and Internet 100 (step 316). With reference to FIG. 3, modem 68 preferably connects uploader system 50 to Internet 100. In this regard modem 68 is any hardware or software which is configured to translate between the digital information sent from processor 52 of uploader system 50 to the analog domain of a telephone system. In a preferred embodiment, modem 68 converts serial digital data from serial port 66 into analog signals suitable for transmission over telephone lines. Modem 68 is any commonly available modem having established standards used by a number of modem manufacturers such as, for example, a commercially available modem manufactured by Rockwell. Point-to-point Protocol (PPP) 64 software establishes communication with modem 68. PPP is a standard which enables multiple network protocols to be used over a modem line or other serial connection. One skilled in the art will appreciate that other commonly known standards for enabling multiple network protocols to be used over a modem line can alternatively be used. PPP software 64 is suitably configured and initialized by known methods for communication with processor 52 and modem 68.

TCP/IP 62 is a widely used network protocol which controls the routing of data and the transfer of data, thereby providing a common means of interconnection through packet transfer devices known as gateways. After processor 52 sends data to TCP/IP 62, TCP/IP 62 encapsulates the data into segments called TCP packets with header information. The header information tracks, checks and orders the data segments in the proper sequence, thereby helping to assure packet delivery, integrity and sorting order. TCP/IP 62 records the acceptance of error-free segments by host server 110. If a segment is not timely acknowledged, TCP/IP 62 re-transmits the packet. The TCP packets are transmitted to an Internet protocol which arranges the segments into Internet protocol packets which contain an IP header wherein the IP header includes address information which enable the gateways to route the IP packet to its proper destination. The IP header contains the source and destination Internet addresses, thereby enabling gateways to properly route the data. One of ordinary skill in the art will appreciate that any initialization and configuration procedures can be used to incorporate TCP/IP 62 into uploader system 50.

Referring again to FIGS. 3 and 9, after connecting to Internet 100, processor 52 launches an FTP program 58 called FETCH produced by The Trustees of Dartmouth College. Processor 52 then provides FETCH with information needed to identify and route the data file, namely the user identification, password, FTP location and data file name (step 318). After appropriate verification procedures between uploader system 50 and host server 110, FETCH uploads the selected data file containing the patient information, full images and thumbnail images by transmitting the data file to host server 110 (step 320). If the transmission is successful (as determined by known in the art procedures discussed above), the file is renamed by deleting the exclamation point (!) from the beginning of the file name (step 322). By deleting the ! after a successful transmission, any incomplete or problem files can be easily identified and deleted (as discussed below). After completing the transmission of information over Internet 100, uploader system 50 automatically terminates the connection to internet 100 (step 324). For confidentiality and security purposes, in a preferred embodiment, all images are uploaded by uploader system 50 to host server 110 are automatically erased after twenty-four hours. One of ordinary skill in the art will appreciate that the automatic deletion feature can be configured for different time periods for different medical facilities, depending on the medical facility preference.

With reference to FIG. 5, during the downloading process from camera system 10 to uploader system 50 and during the uploading process from uploader system 50 to host server 110, log field 184 suitably records and displays most actions in real time, thereby allowing the operator to ensure accurate system performance. To clear Log Field 184, the operator can select the Clear Log Command 186 which suitably deletes the display entries from Log Field 184. Moreover, Settings Command 188 on screen display 170 allows the operator to adjust various known in the art computer display and interface connections. For example, the operator can change the interface connection setting from a direct connection to a PPP connection. In a preferred embodiment, to reduce user manipulation of system 5, the operator does not have access to the Settings Command 188; but instead, the operator is required to call the operator of host server 110 to request access to Settings Command 188. Upon approval, host server 110 suitably allows the medical facility operator to adjust particular settings of system 5.

System 5 includes password protection on multiple levels. Referring again to FIG. 1, when the operator of the medical facility uploads images to host server 110 using uploader system 50, uploader system 50 preferably transmits an appropriate password to host server 110 for verification by host server 110 before host server uploads images transmitted by uploader system 50. Moreover, system 5 is suitably configured to allow the operator to limit the access to the web page created by uploader system 50 to particular physicians or other users. An operator may add a new physician which is entitled to access the web page by providing the physician with a temporary or permanent-temporary password. A permanent-temporary password allows users to become permanent users for that particular medical facility. One time temporary passwords may only be used for accessing the web page once for a particular medical facility.

With reference to FIGS. 1 and 5, Fax More, Permanent Passwords command 178 provides a convenient procedure for supplying additional temporary-permanent physician passwords for distribution by the medical facility operator. More specifically, the medical facility operator initially determines particular physicians which the medical facility approves having repeated access to the particular medical facilities' patient information. After selecting Fax More Permanent Passwords Command 178, for security reasons, uploader system 50 requests entry of the operator's password. After the operator enters a pre-assigned password and host server 110 verifies the operator's password, host server 110 transmits a request to a processor to generate a list of physician temporary-permanent passwords for a particular medical facility and to fax the list to the medical facility which requested the physician passwords. In a preferred embodiment, thirty-two new physician passwords are generated and distributed in response to each request. The medical facility operator then communicates the passwords to authorized physicians. One skilled in the art will appreciate that system 5 may suitably limit the request, retrieval and allocation of physician passwords to administrators of the medical facility by requiring special administrator passwords.

The physician passwords only provide access to the certain patient data at a particular medical facility. Moreover, the physician passwords and IDs are initially temporary. An exemplary temporary physician password is "4123" and temporary user ID is "TEMP1234." One skilled in the art will appreciate that the user passwords and IDs may be any combination of numbers, letters, symbols and/or the like. After the physician enters a temporary user ID and temporary-permanent password into physician computer 150, the temporary user ID and temporary-permanent password is suitably transmitted to host server 110. Host server 110 verifies the temporary-permanent password against an existing list of authorized passwords and requests entry of the physician's social security number, name and address. Host server 110 then re-assigns the physician's social security number as the new permanent physician user ID and requests the physician to enter a new permanent password, if desired. In a preferred embodiment, the physician can select a new permanent password having 4–8 characters. After receiving the physician's new password selection, host server 110 records the new password in association with the physician user ID and the new password is now the physician's permanent password. However, a physician who is registered as a user of one site cannot view images of another site unless the physician is also a registered user of the second site. Because physicians are often registered with more than one medical facility, the physician can receive a different temporary password from another medical facility, and upon following the same procedure as set forth above, the physician can change all temporary passwords from different medical facilities to the same permanent password for all medical facilities. In this regard, the password allocation and replacement routine of the present invention reduces physician confusion and simplifies physician interaction with the system.

Alternatively, the operator can select Fax More One-Time Passwords command 180 which will generate and fax a list of temporary. passwords to the medical facility. This list of passwords is communicated to physicians; however, the physician can only use these temporary password's to access the records of a particular medical facility within system 5 one time. More specifically, the medical facility determines particular physicians which' should have access for a 24-hour period to the particular' medical facilities' patient information. After selecting Fax More Permanent Passwords command 178, uploader system 50 requests, similar to above, entry of the operator's password. After the operator enters a pre-assigned password and host server 110 verifies the operator's password, host server 110 transmits a request to a processor to generate a list of temporary physician passwords for a particular medical facility and to fax the list to the medical facility which requested the physician passwords. In a preferred embodiment, thirty-two new temporary physician passwords are generated and distributed in response to each request. The medical facility operator then communicates the temporary passwords to authorized physicians. Upon entry of a temporary user ID, such as, for example, "1TEMP1234," and temporary password into physician computer 150, the special user ID and temporary password is transmitted to host server 110. Host server 110 verifies the temporary password (but does not change the user ID or password as above), then the system allows the physician to view certain patient data in the particular medical facilities' patient information data file. After the physician exits the particular medical facilities' patient information, the temporary password is deleted from the authorized password list in host server 110.

After receiving a user ID and password as set forth above, the physician can access the patient information in host server 110. Referring to FIG. 1, host server 110 is any hardware or software suitably configured to accept data files from uploader system 50 and to allow the physician's web browser 156 to access information from host server 110. Host server 110 is preferably an Apple Macintosh® server in response to a request by the physician's web browser 156, host server 110 transmits Hypertext Markup Language (HTML) pages through Internet 100 to physician computer 150. HTML pages describe the information which is on web page 200 sent by the host server 110. When a physician accesses web page 200 (FIG. 7), the HTML page instructs the physician's web browser 156 to display on the computer display 154 various information such as, for example, buttons, text, images, animated real-time loops of images, sounds and/or the like. The HTML page is directly encoded into software located in host server 110 by known in the art commercially available desktop publishing and word processing software for writing the HTML page and other known software is used to encode the page into HTML form. In that regard, web pages 200 contain HTML tags of data which assist the physician's web browser 156 in interpreting HTML page. The HTML page may also include HREF Hypertext references which provide a means for linking to other web pages within host server 110 or anywhere on the Internet 100. After the HTML pages are created, their storage addresses are recorded at host server 110. Thus, when a physician makes a request to view a particular HTML page, host server 110 is responsible for finding the page based on the storage address and sending its contents to the physician's web browser 156.

More particularly, referring to FIGS. 1,6,7 and 10, after the physician enters the Internet address for web page 200 (FIG. 7) located on host server 110 (step 350), physician web browser 156 sends a data packet to host server 110 which is received by the WEBSTAR™ program located in host server 110. The WEBSTAR™ program is commonly available and is distributed by Star Nine, Inc.™. WEBSTAR™ suitably transmits web page 200 information to physician computer 150 and WEBSTAR™ logs the Internet Protocol address of physician computer 150 (step 352). Web page 200 preferably displays a list of medical facilities 205 (FIG. 7) which have previously uploaded patient data to host server 110 (step 354). After the physician selects a medical facility from the list of medical facilities 205, a data packet containing the medical facility request is transmitted to host server 110 (step 356). Host server 110 then transmits a request for the physician's user ID and password to physician computer 150. After the physician enters the appropriate user ID and password information into physician computer 150, a data packet containing the user ID and password is transmitted to host server 110 which validates the user ID and password (step 358).

Host server 110 then transmits the physician's medical facility request to "a program called PATIENT.ACGI (located on host server 110). WEBSTAR™ also suitably interrogates the passwords and preforms various password functions which are known in the art, including the transmission of certain passwords to PATIENT.ACGI. PATIENT.ACGI suitably accesses the selected medical facility folder which contains the individual patient folders 60 (step 360). Each medical facility predetermines an expiration time limit for their own patient folders 60 and the expiration time limit is stored in host server 110. PATIENT.ACGI suitably interrogates each patient folder 60 and compares the patient folder time stamp (which indicates the' time and date the folder was uploaded to host server 110) with the selected medical facility expiration time limit. If the patient folder time stamp is later in time then the medical facility expiration time limit, the patient folder 60 is deleted. Moreover, PATIENT.ACGI suitably interrogates each patient folder name and deletes any folder 60 with a name which contains an exclamation point (!) because, as discussed above, the ! in the patient folder 60 name indicates that the folder may contain corrupted or incomplete data (step 362). After deleting the unwanted patient folders 60, PATIENT.ACGI accesses a pre-established HTML web page having empty patient folder 60 fields. PATIENT.ACGI then populates the patient folder 60 fields with the patient folder 60 information associated with the selected medical facility (step 364). PATIENT.ACGI then transmits the populated HTML web page to WEBSTART™ (step 366), which then transmits the populated HTML web page to physician computer 150 (step 368).

Figure 4:
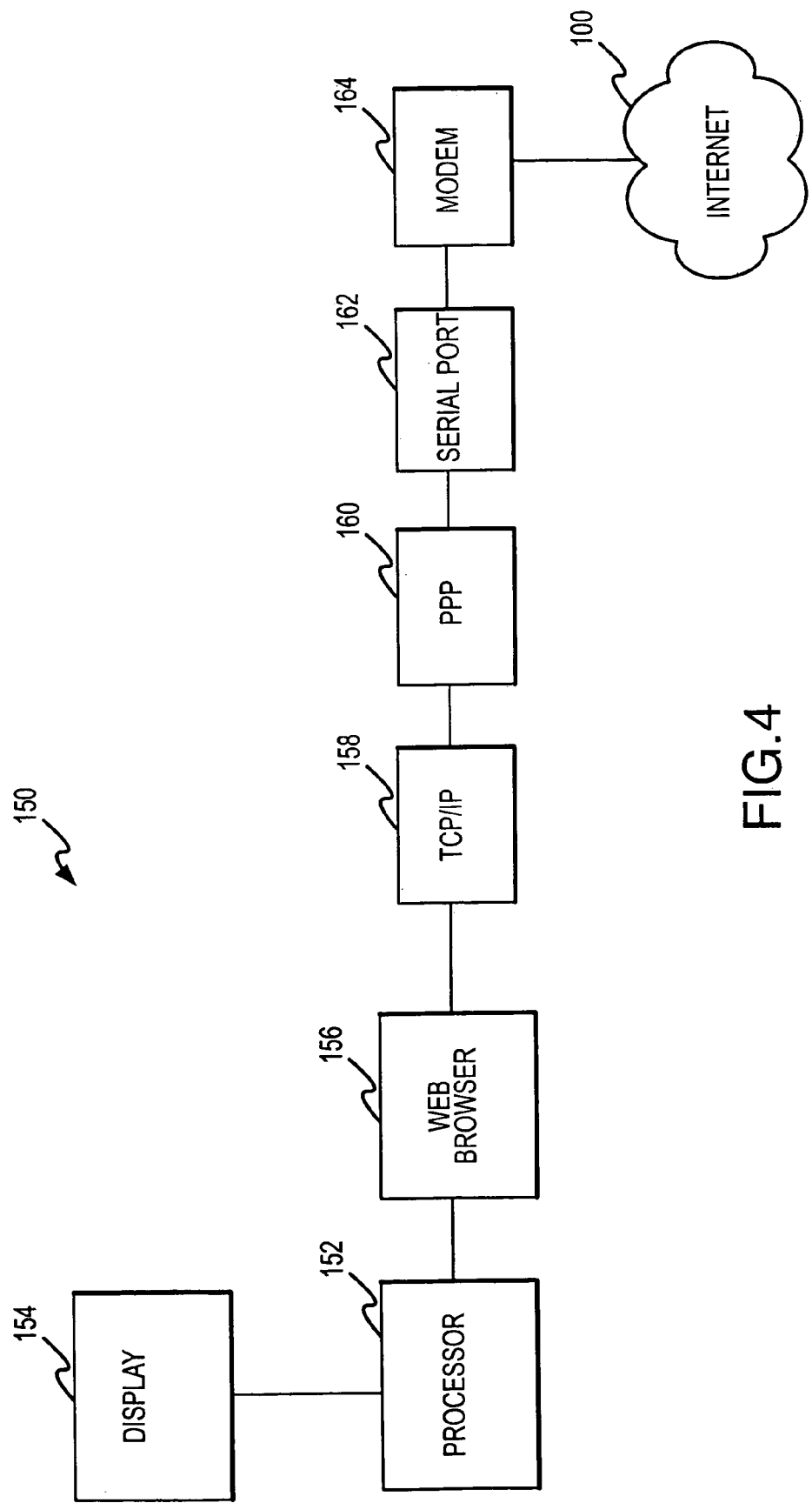
FIG. 4 is an exemplary schematic diagram of the physician computer in more detail.

Physician computer 150 is any system or software suitably configured to access the Internet 100 and browse web page 200 in host server 110. Referring to FIG. 4, physician computer 150 preferably includes processor 152, display 154, web browser 153, TCP/IP 158, PPP 160, serial port 162 and modem 164. A physician suitably requests processor 152 to instruct web browser 156 to access the website located at host server 110. When accessing host server 110 through Internet 100, web browser 156 utilizes TCP/IP 158, PPP 160, serial port 162 and modem 164 in a similar manner as discussed above. Web browser 156 is any commonly known web browser software such as, for example, Netscape®, Microsoft® Internet Explorer®, or the America OnLine® web browser. One skilled in the art will appreciate that there is known in the art browser function's which are incorporated into host server 110 and web browser 156 thereby allowing the physician to manipulate the images, and browse various web pages at the website.

After receiving the populated HTML web page, physician computer 150 displays the HTML web page for the selected medical facility on display 154. The physician then views all of the patient folder 60 names which are available and selects a particular patient name from which the physician can view the selected patient's images (step 370). A data packet containing the patient selection is suitably transmitted to host server 110. After receiving the patient selection data packet, host server 110 suitably transmits the patient selection information to a program called GETPATIENT.ACGI. In a preferred embodiment, GETPATIENT.ACGI also TRANSMITS all physician entries to a log database which logs all physicians which view a particular patient folder 60 (step 372). GETPATIENT.ACGI interrogates the patient folder 60 corresponding to the selected patient and searches for an INDEX.HTML file which indicates that the patient folder 60 has previously been viewed. If the INDEX.HTML file exists, GETPATIENT.ACGI transmits the selected patient folder 60 to WEBSTARTM™ (step 376) which then transmits patient folder 60 to the physician web browser 156 (step 378) (see FIG. 6). If GETPATIENT.ACGI does not find an INDEX.HTML file in patient folder 60, GETPATIENT.ACGI generates an INDEX.HTML file (step 374).

Host server 110 also responds to specific requests of web browser 156, such as performing a specific action including, for example, a request to increase the size of an image on web page 58. One skilled in the art will appreciate that host server 110 is configured with various security features. For example, a configuration file may control the access of a particular physician to certain web pages. Furthermore, physician access may be limited to specific drives, directories and files and a physician may be restricted from inputting data into a web page. In other words, web page 58 is a read only web page. One of ordinary skill in the art will also appreciate that host server 110 may restrict access to certain physicians and other users based upon requested user ID numbers and passwords.

While the present invention has been described in conjunction with preferred and alternative embodiments set forth in the drawing Figures and the specification, it will be appreciated that the invention is not so limited. Various modifications in the selection and arrangement of components, interfaces and process steps may be made without departing from the spirit and 'scope of the invention as set forth in the appended claims.

I claim:

1. A system for secure transmission of data from a facility to a centralized host server for remote viewing from a personal computer, said system comprising:

a camera device;

an uploader device configured to acquire information from said camera device, said uploader device configured to automatically transmit information over a network, said host server configured to communicate with a plurality of said uploader devices through said network, wherein said host server is configured to construct and transmit to said personal computer a web page containing a list of available medical facilities and a list of patient images from each of said medical facilities; and, said personal computer configured to communicate with said host server.

2. The system of claim 1 wherein said camera device is a digital camera.

3. The system of claim 1 wherein said network is at least one of a public, packet-switched Internet and an Ethernet.

4. The system of claim 1 wherein said information includes text and images of a patient.

5. The system of claim 4 wherein said images of patient include at least one of radiological images, x-rays, MR images, CT images, direct pictures of patient pathology, lab data, EKG data, documents and images capable of being photographed by a camera.

6. The system of claim 1 wherein said host server requests a user identification and password from said personal computer; said user identification and password being identical when accessing any of said information.

7. The system of claim 1, wherein said password is at least one of a temporary password and temporary-permanent password.

8. The system of claim 1 wherein said facility is at least one of a hospital, clinic, emergency room, film room, x-ray facility, medical office and sports facility.

9. The system of claim 1 wherein said uploader device is removably connected to said camera device.

10. A system for secure transmission of data from a facility to a centralized host server for remote viewing from a personal computer, said system comprising:
  a camera device;
  an uploader device configured to acquire information from said camera device, said uploader device configured to automatically transmit information over a network,
  said host server configured to communicate with a plurality of said uploader devices through said network, wherein said host server is configured to automatically transmit to said facility a list of new passwords upon a request by said uploader device; and,
  said personal computer configured to communicate with said host server.

11. A method for securely transmitting data acquired by a camera device to a centralized host server for remote viewing from a personal computer, said method comprising:
  acquiring and digitizing images using said camera device;
  transmitting images to an uploader device;
  transmitting said images to said host server via a network by:
    entering text including at least one of patient name and patient history
  into said uploader device;
    requesting a transfer of images;
    counting said images;
    compressing said images if image file is greater than a predetermined
  threshold;
    generating thumbnail image representations of said images;
    populating a data file including said images, thumbnail image representations and associated text entries at said uploader device;
    establishing a network connection;
    transmitting data file to said host server; and,
    terminating said network connection assembling a web page, including said Images, at said host server in response to a request from said personal computer; and,
  transmitting said web page to said personal computer.

12. A method for securely transmitting data acquired by a camera device to a centralized host server for remote viewing from a personal computer, said method comprising:
  acquiring and digitizing images using said camera device;
  transmitting images to an uploader device;
  transmitting said images to said host server via a network;
  assembling a web page, including said images, at said host server in response to a request from said personal computer;
  transmitting said web page to said personal computer, wherein said steps of assembling said web page and transmitting said webpage include:
    establishing a network connection at said personal computer;
    entering host server network address at said personal computer;
    transmitting list of medical facilities from said host server to said personal computer;
    selecting a medical facility at said personal computer;
    validating user identification and password entered at said personal computer;
    accessing, at said host server, patient folders associated with said selected medical facility;
    populating, at said host server, an HTML web page with said patient folders;
    transmitting said HTML web page from said host server to said personal computer;
    selecting, at said personal computer, one of said patient folders in said HTML web page; and,
    transmitting said selected one of said patient folders to said personal computer, wherein said patient folder includes said images.

13. A method for securely transmitting data acquired by a camera device to a centralized host server for remote viewing from a personal computer, said method comprising:
  a) acquiring and digitizing images using said camera device;
  b) transmitting images to an uploader device;
  c) transmitting said images to said host server via a network;
  d) assembling a web page, including said Images, at said host server in response to a request from said personal computer;
  e) transmitting said web page to said personal computer
  f) requesting, at said uploader device, temporary-permanent passwords for a particular medical facility for users of said personal computers;
  g) distributing said temporary-permanent passwords to said users;
  h) requesting, at said personal computer, entry of said temporary-permanent password;
  i) requesting entry, at said personal computer, of a new password;
  j) replacing said temporary-permanent password with said new password; and,
  k) repeating steps (f)–(j) for a different medical facility such that said new password is identical for each of said medical facility.

* * * * *

UNITED STATES PATENT AND TRADEMARK OFFICE
CERTIFICATE OF CORRECTION

PATENT NO. : 7,180,624 B2 Page 1 of 1
APPLICATION NO. : 10/766232
DATED : February 20, 2007
INVENTOR(S) : Kishore Tipirneni It is certified that error appears in the above-identified patent and that said Letters Patent is hereby corrected as shown below:

\*\*On the Title page, Item (63), please delete "Dec. 13, 1998" and insert --Dec. 23, 1998--\*\*

Signed and Sealed this

Twenty-seventh Day of May, 2008

JON W. DUDAS
*Director of the United States Patent and Trademark Office*